(12) United States Patent
deVries et al.

(10) Patent No.: US 8,415,331 B2
(45) Date of Patent: Apr. 9, 2013

(54) DOXYCYCLINE METAL COMPLEX IN A SOLID DOSAGE FORM

(75) Inventors: Tina deVries, Long Valley, NJ (US); Lynn Gold, Seattle, WA (US)

(73) Assignee: Warner Chilcott Company, LLC, Fajardo, PR (US)

( * ) Notice: Subject to any disclaimer, the term of this patent is extended or adjusted under 35 U.S.C. 154(b) by 0 days.

(21) Appl. No.: 12/338,491

(22) Filed: Dec. 18, 2008

(65) Prior Publication Data

US 2011/0171299 A1 Jul. 14, 2011

Related U.S. Application Data

(62) Division of application No. 10/896,045, filed on Jul. 22, 2004, now Pat. No. 7,485,319.

(60) Provisional application No. 60/490,136, filed on Jul. 25, 2003.

(51) Int. Cl.
*A61K 31/65* (2006.01)
*A61K 9/48* (2006.01)
*A61K 9/20* (2006.01)

(52) U.S. Cl.
USPC ............................ 514/152; 424/451; 424/464

(58) Field of Classification Search .................. None
See application file for complete search history.

(56) References Cited

U.S. PATENT DOCUMENTS

| | | |
|---|---|---|
| 2,736,725 A | 2/1956 | Ritter |
| 2,903,395 A | 9/1959 | Salivar |
| 3,122,578 A | 2/1964 | Remmers et al. |
| 3,140,232 A | 7/1964 | Noseworthy |
| 3,459,858 A | 8/1969 | Granatek et al. |
| 3,586,483 A | 6/1971 | Heider et al. |
| 3,674,859 A | 7/1972 | Beutel et al. |
| 3,927,094 A | 12/1975 | Villax |
| 3,932,490 A | 1/1976 | Fernandez |
| 4,038,315 A | 7/1977 | Tobkes |
| 4,061,676 A | 12/1977 | Villax |
| 4,086,332 A | 4/1978 | Armstrong |
| 4,126,680 A | 11/1978 | Armstrong |
| 4,207,258 A | 6/1980 | Broggi et al. |
| 4,418,060 A | 11/1983 | Kahán née László et al. |
| 4,500,458 A | 2/1985 | Villax et al. |
| 4,597,904 A | 7/1986 | Page |
| 4,693,997 A | 9/1987 | Bergwitz-Larsen et al. |
| RE32,535 E | 10/1987 | Villax et al. |
| 4,952,402 A | 8/1990 | Sparks et al. |
| 4,973,719 A | 11/1990 | Khanna et al. |
| 5,167,964 A | 12/1992 | Muhammad et al. |
| 5,188,836 A | 2/1993 | Muhammad et al. |
| 5,211,958 A | 5/1993 | Akkerboom et al. |
| 5,283,065 A | 2/1994 | Doyon et al. |
| 5,464,632 A | 11/1995 | Cousin et al. |
| 5,516,531 A | 5/1996 | Makino et al. |
| 5,538,954 A | 7/1996 | Koch et al. |
| 5,780,055 A | 7/1998 | Habib et al. |
| 5,908,838 A | 6/1999 | Gans |
| 6,077,533 A | 6/2000 | Oshlack et al. |
| 6,077,822 A | 6/2000 | Dyrsting et al. |
| 6,080,426 A | 6/2000 | Amey et al. |
| 6,245,350 B1 | 6/2001 | Amey et al. |
| 6,506,402 B1 | 1/2003 | Winstrom |
| 6,730,320 B2 | 5/2004 | Rudnic et al. |
| 6,841,546 B2 | 1/2005 | Draper et al. |
| 6,958,161 B2 | 10/2005 | Hayes et al. |
| 7,008,631 B2 | 3/2006 | Ashley |
| 7,014,858 B2 | 3/2006 | Ashley |
| 7,063,862 B2 | 6/2006 | Lin et al. |
| 7,087,243 B2 | 8/2006 | Edgren et al. |
| 7,211,267 B2 | 5/2007 | Ashley |
| 7,232,572 B2 | 6/2007 | Ashley |
| 2002/0010162 A1 | 1/2002 | Fleischmajer |
| 2002/0151527 A1 | 10/2002 | Wiegand et al. |
| 2002/0198176 A1 | 12/2002 | Fleischmajer |
| 2003/0077301 A1 | 4/2003 | Maibach et al. |
| 2003/0082120 A1 | 5/2003 | Milstein |
| 2003/0091630 A1 | 5/2003 | Louie-Helm et al. |

(Continued)

FOREIGN PATENT DOCUMENTS

| | | |
|---|---|---|
| EP | 0096942 | 3/1986 |
| GB | 845649 | 8/1960 |

(Continued)

OTHER PUBLICATIONS

Definition of "complex." Merriam-Webster Online Dictionary. www.merriam-webster.com/dictionary/complex (downloaded Jul. 14, 2011).*
Definition of "salt." Merriam-Webster Online Dictionary. www.merriam-webster.com/dictionary/salt (downloaded Jul. 14, 2011).*
CAS Registry No. 564-25-0 (Nov. 16, 1984).*
M. Brion, et al., "Metal Ion-Tetracyclines Interactions in Biological Fluids," Inorganica Chimica Acta, vol. 55, 1981, pp. 47-56, XP002310486.
L.A. Mitscher, et al., "Interaction of Various Tetracyclines with Metallic Cations in Aqueous Solutions as Measured by Circular Dichroism," Antimicrobial Agents Chemother., 1969, vol. 9, pp. 111-115.

(Continued)

*Primary Examiner* — Daniel Sullivan
*Assistant Examiner* — Peter Anthopolos
(74) *Attorney, Agent, or Firm* — Fitzpatrick, Cella, Harper & Scinto

(57) ABSTRACT

The present invention is a solid dosage form of a doxycycline metal complex. The present invention also includes a process for making a doxycycline metal complex in a solid dosage form. The process comprises the steps of (i) providing an aqueous solution of doxycycline or a physiologically acceptable salt thereof; (ii) admixing a metal salt with the aqueous solution; (iii) admixing a base to increase the pH of the aqueous solution, thereby forming a suspension of doxycycline metal; and (iv) drying the suspension, thereby forming a dry granulation of doxycycline metal complex.

8 Claims, No Drawings

U.S. PATENT DOCUMENTS

| | | |
|---|---|---|
| 2003/0092682 A1 | 5/2003 | Heesch |
| 2003/0104052 A1 | 6/2003 | Berner et al. |
| 2003/0133982 A1 | 7/2003 | Heimlich et al. |
| 2003/0133985 A1 | 7/2003 | Louie-Helm et al. |
| 2003/0171340 A1 | 9/2003 | Isbister |
| 2003/0199480 A1 | 10/2003 | Hayes et al. |
| 2003/0211156 A1 | 11/2003 | Dansereau et al. |
| 2003/0229055 A1 | 12/2003 | Ashley |
| 2004/0029843 A1 | 2/2004 | Lawter |
| 2004/0063674 A1 | 4/2004 | Levy et al. |
| 2004/0091529 A1 | 5/2004 | Edgren et al. |
| 2004/0096497 A1 | 5/2004 | Ponder et al. |
| 2004/0101568 A1 | 5/2004 | Bruna et al. |
| 2004/0115261 A1 | 6/2004 | Ashley |
| 2004/0142035 A1 | 7/2004 | Chang et al. |
| 2004/0147492 A1 | 7/2004 | Ashley |
| 2004/0228912 A1 | 11/2004 | Chang et al. |
| 2004/0228915 A1 | 11/2004 | Noack et al. |
| 2004/0258748 A1 | 12/2004 | Madan et al. |
| 2004/0265372 A1 | 12/2004 | Wynn et al. |
| 2004/0265373 A1 | 12/2004 | Wynn et al. |
| 2005/0020545 A1 | 1/2005 | Draper et al. |
| 2005/0037071 A1 | 2/2005 | Cao et al. |
| 2005/0065100 A1 | 3/2005 | Wiegand et al. |
| 2005/0112214 A1 | 5/2005 | Wiegand et al. |
| 2005/0148552 A1 | 7/2005 | Ryan et al. |
| 2005/0153943 A1 | 7/2005 | Ashley |
| 2005/0158377 A1 | 7/2005 | Popp |
| 2005/0163836 A1 | 7/2005 | Fekete et al. |
| 2005/0169986 A1 | 8/2005 | Tian et al. |
| 2005/0196438 A1 | 9/2005 | Wang et al. |
| 2005/0202082 A1 | 9/2005 | Hibino et al. |
| 2006/0003971 A1 | 1/2006 | Nelson |
| 2006/0010010 A1 | 1/2006 | Wiegand et al. |
| 2006/0018933 A1 | 1/2006 | Vaya et al. |
| 2006/0057073 A1 | 3/2006 | Lintz et al. |
| 2006/0062844 A1 | 3/2006 | Chenevier et al. |
| 2006/0078582 A1 | 4/2006 | Kang et al. |
| 2006/0094697 A1 | 5/2006 | Ashley |
| 2006/0134199 A1 | 6/2006 | Suga et al. |
| 2006/0141054 A1 | 6/2006 | Piccariello |
| 2006/0154901 A1 | 7/2006 | Pflugfelder et al. |
| 2006/0183719 A1 | 8/2006 | deVries et al. |
| 2006/0194773 A1 | 8/2006 | Levy et al. |
| 2006/0293290 A1 | 12/2006 | Wortzman et al. |
| 2007/0048373 A1 | 3/2007 | Chastain et al. |
| 2007/0071822 A1 | 3/2007 | Dansereau et al. |
| 2007/0110804 A1 | 5/2007 | Royer |
| 2007/0122471 A1 | 5/2007 | Murakawa et al. |
| 2007/0128269 A1 | 6/2007 | Gervais et al. |
| 2007/0128272 A1 | 6/2007 | Zerbe et al. |
| 2007/0148211 A1 | 6/2007 | Altreuter et al. |
| 2007/0148229 A1 | 6/2007 | Vergnault et al. |
| 2007/0196481 A1 | 8/2007 | Amidon et al. |
| 2007/0225262 A2 | 9/2007 | Wortzman et al. |
| 2007/0231384 A1 | 10/2007 | Ponder et al. |
| 2007/0254023 A1 | 11/2007 | Kiselev et al. |
| 2007/0275933 A1 | 11/2007 | Wortzman et al. |
| 2008/0014257 A1 | 1/2008 | He et al. |
| 2008/0038338 A1 | 2/2008 | Smith et al. |
| 2008/0070873 A1 | 3/2008 | Alekshun et al. |
| 2008/0107780 A1 | 5/2008 | Kresevic et al. |
| 2008/0171727 A1 | 7/2008 | Ashley |
| 2008/0188445 A1 | 8/2008 | Muldoon et al. |
| 2008/0188446 A1 | 8/2008 | Muldoon et al. |
| 2008/0200533 A1 | 8/2008 | Krishnan |
| 2008/0233206 A1 | 9/2008 | Chomczynski |
| 2008/0248107 A1 | 10/2008 | Pilgaonkar et al. |
| 2008/0248124 A1 | 10/2008 | Eguchi et al. |
| 2008/0312168 A1 | 12/2008 | Pilgaonkar et al. |
| 2008/0317841 A1 | 12/2008 | Grenier et al. |
| 2009/0004281 A1 | 1/2009 | Nghiem et al. |
| 2009/0011006 A1 | 1/2009 | Chang et al. |
| 2009/0053310 A1 | 2/2009 | Pilgaonkar et al. |
| 2009/0110728 A1 | 4/2009 | Rastogi et al. |
| 2009/0136568 A1 | 5/2009 | Lukas |
| 2009/0220611 A1 | 9/2009 | Dargelas et al. |
| 2010/0022483 A1 | 1/2010 | Berniac et al. |
| 2010/0055180 A1 | 3/2010 | Deorkar et al. |

FOREIGN PATENT DOCUMENTS

| | | |
|---|---|---|
| GB | 947601 | 1/1964 |
| GB | 1360998 | 7/1974 |
| GB | 2088864 | 6/1982 |
| RU | 2191573 C1 | 10/2002 |
| WO | 98/56360 A2 | 12/1998 |
| WO | 02/080932 A1 | 10/2002 |
| WO | 2004000223 | 12/2003 |
| WO | 2004/091483 A2 | 10/2004 |
| WO | 2005011707 | 2/2005 |
| WO | 2008/104993 A1 | 9/2008 |

OTHER PUBLICATIONS

Y. Baozhen, et al., "Studies on the Complexation of Doxycycline Hyclate With Some Metallic Cations and Its Stability in the Aqueous Solution," Acta Acad. Med. Sichuah, 1983, pp. 14 and 26-30. (Translation Included).

L.Z. Benet, et al., "Thermodynamics of Chelation by Tetracyclines," Journal of Pharmaceutical Sciences, vol. 55, No. 11, Nov. 1966, pp. 1184-1190.

J. L. Colaizzi, et al., "Biophysical Study of the Mode of Action of the Tetracycline Antibiotics," Journal of Pharmaceutical Sciences, vol. 54, No. 10, Oct. 1965, pp. 1425-1436.

K.H. Ibsen, et al., "Complexes of Calcium and Magnesium with Oxytetracycline," Proc. Soc. Exp. Biol. Med., Apr. 1962, vol. 109, pp. 797-801.

J.T. Doluisio, et al., "Metal Complexation of the Tetracycline Hydrochlorides," J. Med. Chem., Jan. 1963, vol. 6, pp. 16-21.

G. Berthon, et al., "Metal Ion-Tetracycline Interactions in Biological Fluids. 2. Potentiometric Study of Magnesium Complexes with Tetracycline, Oxytetracycline, Doxycycline, and Minocycline, and Discussion of their Possible Influence on the Bioavailability of these Antibiotics in Blood Plasma," Journal of Inorganic Biochemistry, vol. 19, 1983, pp. 1-18.

J.D. Smilack, "The Tetracyclines," Mayo Clin. Proc. vol. 74, 1999, pp. 727-729.

Y. Liang, et al., "Stability Studies of tetracycline in methanol solution," Journal of Chromatography A., vol. 827, 1998, pp. 45-55.

F.C. Machado, et al., "Metal Complexes of Anhydrotetracycline. 2. Absorption and Circular Dichroism Study of Mg(II), Al(III), and Fe(III) Complexes. Possible Influence of the Mg(II) Complex on the Toxic Side Efffects of Tetracycline," Journal of Inorganic Biochemistry, vol. 60, 1995, pp. 163-173.

P. Orth, et al., "Tetracycline-Chelated Mg2+ Ion Initiates Helix Unwinding in Tet Repressor Induction," Biochemistry, vol. 38, No. 1, 1999, pp. 191-198.

M.C. Saux, et al., "Pharmacokinetic study of doxycycline polyphosphate (PPD), Hydrochloride (CHD) and base (DB)," European Journal of Drug Metabolism and Pharmacokinetics, vol. 6, No. 1, 1981, pp. 3-10.

M. Novak-Pekli, et al., "Equilibrium studies on tetracycline-metal ion systems," Journal of Pharmaceutical and Biomedical Analysis, vol. 14, 1996, pp. 1025-1029.

N. Sultana, et al., "Effect of Antacids on the Dissolution Behavior of Methacycline and Doxycycline," J.P.M.A., 1984, pp. 59-63.

S. Berge, et al., "Pharmaceutical Salts," Journal of Pharmaceutical Sciences, vol. 66, No. 1, 1977, pp. 1-19.

A.M. Ristuccia, et al., "Current Concepts in Antimicrobial Therapy of Prostatitis," Urology, vol. XX, No. 3, 1982, pp. 338-345.

J.B. Bogardus, et al., "Dissolution Rates of Doxycycline Free Base and Hydrochloride Salts," Journal of Pharmaceutical Sciences, vol. 68, No. 9, 1979, pp. 1183-1184.

D.T. Cooke, et al., "Temperature and concentration dependent partitioning of three tetracyclines between phosphate buffers and octanol," J. Pharm. Pharmac., vol. 29, 1977, pp. 190-191.

J.B. Bogardus, et al., "Solubility of Doxycycline in Aqueous Solution," Journal of Pharmaceutical Sciences, vol. 68, No. 2, 1979, pp. 188-194.

E.J. Antai, et al., "Bioequivalency of Doxycycline Products," Journal of Pharmaceutical Sciences, vol. 64, No. 12, 1975, pp. 2015-2018.

W.A. Baker, Jr. et al., "Metal Binding in Tetracyclines. Cobalt (II) and Nickel (II) Complexes," Journal of the American Chemical Society, 88:6, Mar. 20, 1966, pp. 1314-1317.

A.H. Caswell, et al., "Selectivity of Cation Chelation to Tetracyclines: Evidence for Special Conformation of Calcium Chelate," Biochemical and Biophysical Research Communications, vol. 43, No. 3, 1971, pp. 625-630.

T.K. Katakwar, et al., "Synthesis and Characterisation of Tetracycline Hydrochloride and Doxycycline-Hydrochloride Complexes with Cu(II) and Zn(II)," Hindustan Antibiotics Bulletin, vol. 26, No. 1 &2, Feb.-May 1984, pp. 2-13.

J.M. Wessels, et al., "The Complexation of Tetracycline and Anhydrotetracycline with Mg2+ and Ca2+: A Spectroscopic Study," J. Phys. Chem. B, vol. 102, No. 46, 1998, pp. 9323-9331.

Barringer, W.C. et al., "Minocycline hydrochloride and its relationship to other tetracycline antibiotics", American Journal of Pharmacy, pp. 179-191 (Nov.-Dec. 1974).

The United States Pharmacopeia, The National Formulary, "Doxycycline Calcium Oral Suspension," USP XXII, p. 480 (1989).

International Union of Pure and Applied Chemistry, "Compendium of Chemical Terminology—Gold Book", Ver. 2.3, definitions of "salt" and "complex" (Oct. 11, 2011).

Office Action in U.S. Appl. No. 11/336,551, issued Nov. 15, 2011.

English translation of Official Action in Japanese Appln. No. 2007-552294, dated Apr. 11, 2012.

Office Action in Canadian Appln. No. 2,595,481, dated Mar. 27, 2012.

Examination Report in New Zealand Appln. No. 556582, dated Oct. 6, 2010.

Examination Report in New Zealand Appln. No. 556582, dated Jun. 26, 2009.

English translation of Office Action in Israeli Appln. No. 184658, dated Dec. 22, 2009.

Office Action in European Appln. No. 06719046.2-2123, dated Jul. 8, 2009.

Office Action in European Appln. No. 06719046.2-2123, dated Jan. 22, 2008.

Examination Report in Australian Appln. No. 2006206359, dated Feb. 22, 2010.

Final Office Action in U.S. Appl. No. 11/336,551 dated Jul. 30, 2012.

* cited by examiner

DOXYCYCLINE METAL COMPLEX IN A SOLID DOSAGE FORM

CROSS-REFERENCE TO RELATED APPLICATIONS

This application is a divisional of application Ser. No. 10/896,045, filed Jul. 22, 2004, which claims the benefit of U.S. Provisional Application No. 60/490,136, filed Jul. 25, 2003. The entire contents of all of the above mentioned applications are incorporated herein by reference.

BACKGROUND OF THE INVENTION

1. Field of the Invention

The present invention is directed to a doxycycline metal complex. More particularly, the present invention is directed to a solid dosage form of a doxycycline metal complex.

2. Related Background Art

Doxycycline (6-deoxy-5-hydroxytetracycline monohydrate) is a broad spectrum bacteriostatic compound that is effective against gram-positive, gram-negative, aerobic and anaerobic bacteria, as well as spirochetes, mycoplasmas, rickettsiae, chlamydiae and some protozoans. It works by inhibiting protein synthesis in bacteria or protozoans, which effectively kills them. It is commonly used in the treatment of bacterial infections caused by these organisms, such as urinary tract infections, upper respiratory tract infections, acne, gonorrhea, chlamydia, anthrax, lyme disease and others.

Individuals taking doxycycline, are advised that iron supplements, multivitamins, calcium supplements, antacids, or laxatives should be avoided. These products can adversely reduce the efficacy of doxycycline by reducing its absorption in the body.

British Patent No. 1,360,998 to Villax describes a process for isolation of α-6-deoxytetracyclines from a crude reaction mixture. The patent also discloses that calcium salts of tetracyclines are suitable for oral preparations such as suspensions. However, calcium salts of doxycycline are known to be particularly unstable in an alkaline pH environment. Moreover, the process described by Villax, uses an organic solvent, i.e., methanol. While organic solvents are often used to prepare pharmaceutically active ingredients, they are generally not desirable in the process of preparing a solid dosage form containing a pharmaceutically active ingredient. Clearly, the process disclosed in Villax for isolating the deoxytetracyclines would not result in a solid dosage form suitable for pharmaceutical administration to humans due to residual solvent.

Doxycycline is a very bitter tasting drug. Currently, a doxycycline metal salt is only available as a suspension of doxycycline calcium. An advantage of the doxycycline calcium complex suspension is that it has an acceptable taste. But many individual's find a liquid dosage form inconvenient. Having no real alternative, i.e., a solid dosage form of a doxycycline metal complex, they must put up with the inconvenience.

Another source of doxycycline is doxycycline hyclate. However, it can cause complications, such as esophageal ulceration. This would not be a problem with a solid dosage form of doxycycline. For example, a doxycycline calcium complex chewable tablet, if available, would not cause ulceration of the esophagus because the drug would not be soluble and therefore would pass through the esophageal environment without harming it.

However, making a solid dosage form of a doxycycline metal complex is extremely difficult. For example, it is not known how to filter a doxycycline metal complex in an aqueous suspension, such as doxycycline calcium complex. Prior art methods have not made it possible to obtain reasonably pure doxycycline metal complex from an aqueous solution.

SUMMARY OF THE INVENTION

The present invention is directed to a solid dosage form of a doxycycline metal complex for pharmaceutical administration.

The present invention includes a solid dosage form of a pharmaceutical composition comprising: (i) a doxycycline metal complex and (ii) one or more pharmaceutically acceptable excipients.

The present invention also includes a process for making a doxycycline metal complex in a solid dosage form. The process comprises the steps of (i) providing an aqueous solution of doxycycline or a physiologically acceptable salt thereof; (ii) admixing a metal salt with the aqueous solution; (iii) admixing a base to increase the pH of the aqueous solution, thereby forming a suspension of doxycycline metal; and (iv) drying the suspension, thereby forming a dry granulation of doxycycline metal complex. Optionally, the process may include the step of admixing one or more pharmaceutically acceptable excipients. The excipient may be added prior to the step of drying the suspension or after the doxycycline metal complex granulation is formed. Moreover, the granulation may be further processed by filling the granulation into capsules or compressing it into tablets.

In another embodiment, the process for making a doxycycline metal complex in a solid dosage form comprises the steps of (i) providing an aqueous solution of doxycycline or a physiologically acceptable salt thereof; (ii) admixing a metal salt with the aqueous solution; (iii) admixing a base to increase the pH of the aqueous solution, thereby forming a suspension of doxycycline metal complex; (iv) admixing one or more pharmaceutically acceptable-excipients with the suspension to absorb water, thereby forming a wet granulation; and (v) drying the wet granulation, thereby forming a dry granulation of doxycycline metal complex. Optionally, the step of admixing one or more pharmaceutically acceptable-excipients may be performed after the wet granulation is formed. In addition, the dry granulation may be further processed by filling the dry granulation into capsules or compressing it into tablets.

In yet another embodiment, the present invention is a method of treating bacterial infections, which comprises the step of administering a safe and effective amount of a doxycycline metal complex in a solid dosage form for an effective time period, to a host in need thereof.

In addition, the invention includes a method for treating ailments resulting from microorganisms and/or bacteria, comprising the step of administering a safe and effective amount of a doxycycline metal complex in a solid dosage form for an effective time period, to a host in need thereof.

DETAILED DESCRIPTION OF THE INVENTION

For the purposes of the present invention, all percentages given denote percent by weight, unless otherwise specified.

The doxycycline metal complex and the active ingredients of the present invention are used in a "safe and effective amount." This is understood to mean a sufficient amount of a compound or composition that will positively modify the symptoms and/or condition to be treated, with the proviso that the amount is low enough to avoid serious side effects. The amount of the compound, e.g., doxycycline metal complex, that is considered safe and effective, will depend upon several factors. For example, one should consider the condition and severity of the condition being treated, the age, body weight, general health, sex, diet, and physical condition of the patient being treated, the duration of the treatment, the nature of concurrent therapy, the particular active ingredient being employed, the particular pharmaceutically-acceptable excipients utilized, the time of administration, method of administration, rate of excretion, drug combination, and any other relevant factors.

The term "pharmaceutically-acceptable excipient" is understood to mean any physiologically inert, pharmacologically inactive material known to one skilled in the art, which is compatible with the physical and chemical characteristics of the particular doxycycline metal complex selected for use.

The present invention is directed to a solid dosage form of a doxycycline metal complex for pharmaceutically acceptable administration to a human, i.e. any residual solvents or other impurities are at a level that is considered safe for human consumption. The doxycycline metal complex may be, for example, doxycycline calcium complex, doxycycline magnesium complex, doxycycline sodium complex, or doxycycline zinc complex. One advantage of the doxycycline metal complex is that it delivers to the user/patient, doxycycline and a mineral source which may be useful. For example, a doxycycline calcium complex tablet would provide the user/patient a source of doxycycline and a source of calcium.

This is contrary to the teachings of the prior art, where it is taught that calcium inhibits the absorption of tetracycline. The inventors, however, have discovered that a therapeutic amount of doxycycline can be absorbed from a doxycycline metal solid, e.g., doxycycline calcium complex in solid dosage form, as taught by the present invention.

Ideally, the doxycycline has undergone complete complexation. This is understood to mean that at least about 75% by weight of the doxycycline is complexed. More preferably at least about 90% has complexed. It should be understood, however, that an excess of doxycycline or metal salt may be added to form the doxycycline metal complex.

It has been hypothesized that the doxycycline metal complex has a metal to doxycycline mole ratio of from about 0.5 to about 3 in the solid dosage form. Preferably the ratio is from about 1.5 to about 2.5, and more preferably about 1:2.

The present invention also includes a pharmaceutical composition formulated together with pharmaceutically acceptable carriers or excipients and/or bioactive agents. The composition comprises (i) a doxycycline metal complex and (ii) one or more pharmaceutically-acceptable excipients.

Preferably, the pharmaceutical composition may take the form of a powder, capsule, tablet, coated tablet, aerosol, pellet, chewable tablet, lozenge, gelatin filled capsule, and the like.

Suitable pharmaceutically-acceptable excipients include, but are not limited to, polymers, resins, plasticizers, fillers, lubricants, binders, disintegrants, granulating agents, solvents, co-solvents, surfactants, preservatives, sweetening agents, flavoring agents, buffering systems, antioxidants, pharmaceutical grade dyes, pigments, and mixtures thereof.

Polymers that may be used, include but are not limited to, hydroxypropylmethylcellulose (HPMC) alone and/or in combination with hydroxypropylcellulose (HPC), carboxymethylcellulose, acrylic resins such as Eudragit®, methylcellulose, ethylcellulose, and polyvinylpyrrolidone or other commercially available film-coating preparations.

Suitable plasticizers, include but are not limited to, polyethylene glycol, propylene glycol, dibutyl phthalate, castor oil, acetylated monoglycerides, triacetin, and mixtures thereof.

Examples of fillers, include but are not limited to, lactose, sucrose, maltodextrin, mannitol, starch, microcrystalline cellulose, and mixtures thereof.

Lubricants that may be used, include but are not limited to, magnesium stearate, stearic acid, talc, and mixtures thereof.

Suitable binders, include but are not limited to, methycellulose, sodium carboxymethycellulose, hydroxypropylmethylcellulose, carbomer, povidone, acacia, guar gum, xanthan gum, tragacanth, calcium silicate, magnesium aluminum silicate, ethylcellulose, pregelatinized starch, and mixtures thereof. Particularly preferred are methycellulose, carbomer, xanthan gum, guar gum, povidone and sodium carboxymethycellulose.

Disintegrants that may be used, include but are not limited to, crospovidone, sodium carboxymethyl starch, sodium starch glycolate, sodium carboxymethyl cellulose, alginic acid, clays, ion exchange resins, and mixtures thereof.

Examples of surfactants, include but are not limited to, polyoxyethylene sorbitan fatty acid esters, polyoxyethylene monoalkyl ethers, sucrose monoesters, lanolin esters and ethers, and mixtures thereof.

Suitable preservatives, include but are not limited to, phenol, alkyl esters of parahydroxybenzoic acid, benzoic acid and the salts thereof, boric acid and the salts thereof, sorbic acid and the salts thereof, chlorbutanol, benzyl alcohol, thimerosal, phenylmercuric acetate and nitrate, nitromersol, benzalkonium chloride, cetylpyridinium chloride, methyl paraben, propyl paraben, and mixtures thereof. Particularly preferred are the salts of benzoic acid, cetylpyridinium chloride, methyl paraben and propyl paraben.

Antioxidants that may be used, include but are not limited to, tocopherols and derivatives thereof, ascorbic acid, beta-carotene, selenium, sodium bisulfite, sodium metabisulfite, ascorbyl palmitate, and mixtures thereof.

Suitable sweeteners, include but are not limited to, sucrose, glucose, saccharin, aspartame, and mixtures thereof. Particularly preferred are sucrose and saccharin.

Buffering systems that may be used include, but are not limited to, potassium acetate, boric carbonic, phosphoric, succinic, malic, tartaric, citric, acetic, benzoic, lactic, glyceric, gluconic, glutaric, glutamic, and mixtures thereof. Particularly preferred are phosphoric, tartaric, citric, and potassium acetate.

Water is preferably used as the solvent. Although other solvents may be used.

Suitable co-solvents, include but are not limited to, ethanol, glycerin, propylene glycol, polyethylene glycol, and mixtures thereof.

The pharmaceutical compositions described herein are comprised of from about 0.1 weight percent (wt. %) to about 99.9 wt. %, preferably from about 5.0 wt. % to about 50.0 wt. %, and most preferably from about 10 wt. % to about 50 wt. % doxycycline metal complex, and from about 0.1 wt. % to about 99.9 wt. %, preferably from about 5.0 wt. % to about 99.9 wt. %, and most preferably from about 50 wt. % to about 90 wt. % of one or more pharmaceutically-acceptable excipients.

The solid dosage form of a doxycycline metal complex is made using a novel process. The process comprises the steps of (i) providing an aqueous solution of doxycycline or a physiologically acceptable salt thereof; (ii) admixing a metal salt to the aqueous solution, (iii) admixing a base to increase the pH of the aqueous solution, thereby forming a suspension of doxycycline metal complex; and (iv) drying the suspension, thereby forming a dry granulation of doxycycline metal complex. Optionally, one or more pharmaceutically acceptable-excipients may be admixed, before, during, or after each processing step.

The doxycycline or physiologically acceptable salt may be, for example, doxycycline hyclate, doxycycline monohydrate, doxycycline carrageenate, doxycycline phosphate, or mixtures thereof. The doxycycline or physiologically acceptable salt is dissolved in an aqueous solution. Any suitable means may be used to dissolve the doxycycline or doxycycline salt in the aqueous solution. Generally, all that is required is some form of mixing. The aqueous solution is preferably comprised of at least about 75 wt. % water. Other components can be included in the aqueous solution such as, for example ethanol. The aqueous solution generally will have a pH that is in a range of about 1 to about 8.

Suitable metal salts include but are not limited to, calcium salts, sodium salts, magnesium salts, zinc salts, and mixtures thereof. A particularly preferred metal salt is calcium chloride. The metal salt is added with or without mixing, but it is generally mixed into solution.

About 1 wt. % to about 50 wt. % of the metal salt is added to the aqueous solution, based on the total weight of the doxycycline formulation. Preferably, the metal salt is about 1 wt. % to about 25 wt. %, more preferably 3 wt. % to about 10 wt. %.

A base is added to the aqueous solution and mixed with the other components. The base is added in an amount effective to form a suspension of the doxycycline metal complex. Generally the addition of the base raises the pH of the solution to a pH range of about 2.5 to about 8. Suitable bases include for example, sodium hydroxide, potassium hydroxide, triethanolamine, diethanolamine, monoethanolamine, sodium bicarbonate, and mixtures thereof.

The amount of base that is added will depend on various factors, including the pH of the aqueous solution and the formation of the suspension. Generally, about 1 wt. % to about 5 wt. % of the base is added, based on the total weight of the doxycycline formulation. More preferably about 2 wt. % to about 4 wt. % of the base is added.

Drying the suspension may be carried out using a variety of techniques. For example in one embodiment, a spray dryer is used and the suspension is sprayed onto an excipient. Other methods include decanting, evaporation, freeze drying, tray drying, fluid-bed drying, and the like.

In another embodiment, the process for making a solid dosage form of a doxycycline metal complex comprises the steps of: (i) providing an aqueous solution of doxycycline or a physiologically acceptable salt thereof; (ii) admixing a metal salt with the aqueous solution, (iii) admixing a base to increase the pH of the solution, thereby forming a suspension of doxycycline metal complex; (iv) admixing one or more pharmaceutically acceptable-excipients with the suspension, thereby forming a wet granulation; and (v) drying the wet granulation, thereby forming a dry granulation of the doxycycline metal complex. Steps (i)-(iii) of this embodiment are the same as the prior described process that forms the solid dosage form from the suspension.

This embodiment, however, utilizes an excipient to assist in forming a wet granulation. The inventors have discovered that an excipient, e.g., microcrystalline cellulose, will absorbed and adsorbed the moisture in the suspension when admixed with the suspension. The result is a wet granulation or slurry that has about 5 wt. % to about 99 wt. % water. Preferably, the moisture in the wet granulation is about 25 wt. % to about 60 wt. %. By forming the wet granulation, the drying process can proceed more readily.

One or more pharmaceutically acceptable-excipients can be admixed in either process during any of the process steps. Moreover, excipients can be added in more than one step.

The wet granulation may be drided by tray-drying, fluid-bed drying, decanting, evaporating, freeze drying, a combination thereof, or by other processes known to those skilled in the art.

It is desirable that the doxycycline metal complex granulation be dried to a moisture content of about 1 wt. % to about 15 wt. % based on the total weight of the doxycycline metal complex granulation. More preferably, the moisture content should be less than about 10 wt. %. Most preferably, to about 1 wt. % to about 6 wt. %.

The resulting doxycycline metal complex is in the form of a dry granulation consisting of granules and powder. The dry granulation may be blended with excipients such as lubricants, i.e. magnesium stearate. The final blend may be further processed, by filling it into capsules.

The inventors have also discovered that the doxycycline metal complex granulation formed after the drying step is well suited for tableting. In fact, should the formulator choose, tableting operations may be performed without the use of additional tableting excipients. Another significant advantage is, unlike other synthesis processes, the method of the present invention does not require a purification step to remove undesirable impurities. This makes the process more efficient and enables tablets to be made directly from the doxycycline metal complex granulation. However, it should be understood that tableting excipients may be incorporated. As previously noted, the excipients, i.e. lubricants, may be added before and/or after the step of drying the suspension or wet granulation. The excipients are simply added and mixed with the other components.

In a preferred embodiment, the tablets are chewable tablets. This would be greatly beneficial to those who suffer from esophageal ulceration, since a chewable tablet of a doxycycline metal complex is not soluble in the esophageal environment. Therefore the chewable tablet would pass through the esophagus in a harmless manner.

In addition, the solid dosage form of the present invention may contain additional ingredients. For example, the additional ingredients may include natural and artificial flavors, sweeteners, colorings, coating excipients, binders, disintegrants, lubricants, and the like.

The solid dosage form is generally orally administrated in the form of tablets, capsules, powders, granules, lozenges, aerosols, pellets, chewable tablets, and the like. Excipents such as binding agents, for example syrup, acacia, gelatin, sorbitol, tragacanth, or polyvinyl-pyrrolidone; fillers for example lactose, sugar, maize-starch, calcium phosphate, sorbitol or glycine; tableting lubricant, for example magnesium stearate, talc, polyethylene glycol or silica; disintegrants for example potato starch, or acceptable wetting agents such as sodium lauryl sulphate, may be included to facilitate the formation of the tablet. In addition, coatings may be applied over the tablets using methods known in the art.

The present invention also includes a method for treating bacterial infections. The method comprises the step of administering to a host, such as a human or animal, a safe and effective amount of a doxycycline metal complex, in solid dosage form. Examples of bacterial infections that can be treated with a doxycycline metal complex, include urinary tract infections, upper respiratory tract infections, acne, gonorrhea, chlamydia, syphilis, anthrax, lyme disease and the like.

The solid dosage form of a doxycycline metal complex may be used in the treatment of ailments caused by bacteria and microorganisms. Non-limiting examples of bacteria and microorganisms are gram-positive microorganisms, gram-negative microorganisms, aerobic bacteria, anaerobic bacteria, spirochetes, mycoplasmas, rickettsiae, chlamydiae, *treponema, listeria, bacillus anthracis, fusobacterium fusiforme, actinomyces israelii, clostridium, ureaplasma urealyticum, borrelia recurrentis, haemophilus ducreyi, yersinia pestis, francisella tularensis, vibrio cholerae, brucella, campylobacter fetus, bartonella bacilliformis, calymmatobacterium granulomatis*, and protozoans. The treatment would require administering a safe and effective amount of a solid dosage form of a doxycycline metal complex for an effective period of time.

EXAMPLE 1

TABLE 1

| Ingredient | % w/w | Total quantity |
| --- | --- | --- |
| Doxycycline hyclate | 16.5 | 830 g |
| Calcium chloride | 5.6 | 280 g |
| Sodium hydroxide | 2.6 | 130 g |
| Microcrystalline cellulose | 74.9 | 3760 g |
| Magnesium stearate | 0.4 | 20 g |

A 20-25% solution of doxycycline hyclate is prepared by dissolving 16.5 g of doxycycline hyclate in water. A 50% solution of calcium chloride is also prepared by dissolving 5.6 g of calcium chloride in water. The doxycycline hyclate solution and calcium chloride solution are combined and mixed in accordance with the amounts specified in TABLE 1.

5N Sodium hydroxide is then added to the mixture. This raises the pH of the mixture to about 5. Preferably the pH is raised to about 6, and most preferably, the pH is raised about 6, but below about 8. This forms a suspension of doxycycline-calcium complex. The doxycycline-calcium complex present in this suspension consists of doxycycline and calcium. The molar ratio of doxycycline to calcium in the complex is 1:1.

An excipient, microcrystalline cellulose (74.9 g), is then added to the suspension. The microcrystalline cellulose absorbs and adsorbs the moisture in the suspension, resulting in the formation of a wet granulation.

The wet granulation is dried using a fluid-bed or tray dryer to reduce the moisture content to less than 10%, and preferably to between about 1% to about 6%, thereby forming a dry granulation.

The dry granulation is milled through a 14-mesh screen.

0.4 g of magnesium stearate is added as a lubricant, to form the final dry granulation.

At this point, a colorant can be added.

The dry granulation can now be used to fill gelatin capsules, or it can be compressed into tablets.

Once the gelatin capsules or tablets are made, a film coating can be applied over the tablets.

EXAMPLE 2

TABLE 2

| Ingredient | % w/w | Total quantity |
| --- | --- | --- |
| Doxycycline hyclate | 19.3 | 2480 g |
| Calcium chloride | 6.5 | 840 g |
| Sodium hydroxide | 3.0 | 380 g |
| Microcrystalline cellulose | 71.0 | 9120 g |
| Magnesium stearate | 0.2 | 30 g |

The procedure of EXAMPLE 1 was followed with the exception that the percent by weight of each ingredient was varied as indicated in TABLE 2 above. As in EXAMPLE 1, the doxycycline-calcium complex present in the suspension of EXAMPLE 2 consists of doxycycline and calcium. The molar ratio of doxycycline to calcium in the complex is 1:1.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A solid dosage form comprising a doxycycline calcium complex for pharmaceutical administration, wherein the complex consists of doxycycline and calcium, and wherein the molar ratio of doxycycline to calcium in the complex is 1:1.

2. The solid dosage form of claim 1, wherein said solid dosage form is selected from the group consisting of powders, granules, tablets, coated tablets, gelatin filled capsules, pellets, and chewable tablets.

3. The solid dosage form of claim 2, wherein said solid dosage form is a chewable tablet.

4. A solid pharmaceutical dosage form comprising:
   (i) a doxycycline calcium complex, wherein the complex consists of doxycycline and calcium in a solid form, and wherein the molar ratio of doxycycline to calcium in the complex is 1:1; and
   (ii) one or more pharmaceutically acceptable excipients.

5. The composition of claim 4, wherein said pharmaceutically acceptable excipient is selected from the group consisting of polymers, resins, plasticizers, fillers, lubricants, binders, disintegrants, granulating agents, solvents, co-solvents, surfactants, preservatives, sweetening agents, flavoring agents, buffering systems, antioxidants, pharmaceutical-grade dyes, pigments, and mixtures thereof.

6. The composition of claim 4, wherein said pharmaceutically acceptable excipient is microcrystalline cellulose.

7. A solid dosage form comprising a doxycycline calcium complex, wherein the complex consists of doxycycline and calcium, wherein the molar ratio of doxycycline to calcium in the complex is 1:1, and wherein the complex was made by a process comprising the steps of:
   (i) providing an aqueous solution of doxycycline or a physiologically acceptable salt thereof;
   (ii) admixing a calcium salt with the aqueous solution;
   (iii) admixing a base to increase the pH of the aqueous solution, thereby forming a suspension of doxycycline calcium complex; and
   (iv) drying the suspension, thereby forming a dry granulation of doxycycline calcium complex.

8. A method of treating a bacterial infection in a subject, the method comprising:
   administering to the subject a solid pharmaceutical dosage form comprising a solid doxycycline calcium complex, wherein the complex consists of doxycycline and calcium, and wherein the molar ratio of doxycycline to calcium in the complex is 1:1.

* * * * *

UNITED STATES PATENT AND TRADEMARK OFFICE
CERTIFICATE OF CORRECTION

| | | |
|---|---|---|
| PATENT NO. | : 8,415,331 B2 | Page 1 of 1 |
| APPLICATION NO. | : 12/338491 | |
| DATED | : April 9, 2013 | |
| INVENTOR(S) | : Tina de Vries et al. | |

It is certified that error appears in the above-identified patent and that said Letters Patent is hereby corrected as shown below:

In the Specification

COLUMN 1:

Line 54, "individual's" should read --individuals--.

COLUMN 2:

Line 37, "acceptable-excipients" should read --acceptable excipients--; and
Line 41, "acceptable-" should read --acceptable--.

COLUMN 4:

Line 43, "boric" should read --boric,--.

COLUMN 5:

Line 64, "absorbed and adsorbed" should read --absorb and adsorb--.

COLUMN 6:

Line 3, "acceptable-excipients" should read --acceptable excipients--;
Line 6, "drided" should read --dried--;
Line 47, "administrated" should read --administered--;
Line 51, "fillers" should read --fillers,--;
Line 53, "lubricant," should read --lubricants,--; and
Line 54, "disintegrants" should read --disintegrants,--.

Signed and Sealed this
Seventeenth Day of June, 2014

Michelle K. Lee
*Deputy Director of the United States Patent and Trademark Office*